United States Patent
Bradshaw et al.

(10) Patent No.: US 6,283,910 B1
(45) Date of Patent: Sep. 4, 2001

(54) METHOD OF TREATING A BODY VESSEL OR DUCT WITH RADIATION FROM WITHIN THE LUMEN

(76) Inventors: Anthony J. Bradshaw, 2938 Kennesaw Dr., Missouri City, TX (US) 77459; Steven L. Weinberg, 821 W. Main St., League City, TX (US) 77573; Albert E. Raizner, Department of Medicine Baylor College of Medicine One Baylor Plz., Houston, TX (US) 77030

( * ) Notice: Subject to any disclaimer, the term of this patent is extended or adjusted under 35 U.S.C. 154(b) by 0 days.

(21) Appl. No.: 08/644,101

(22) Filed: Feb. 7, 1996

Related U.S. Application Data (63) Continuation of application No. 08/057,322, filed on May 5, 1993, now abandoned.

(51) Int. Cl.$^7$ .................................................. A61N 5/00
(52) U.S. Cl. ................................................ 600/3; 600/8
(58) Field of Search ........................... 600/1–8; 128/772

(56) References Cited

U.S. PATENT DOCUMENTS

| | | | |
|---|---|---|---|
| 4,578,061 | 3/1986 | Lemelson | 604/164 |
| 4,815,449 | 3/1989 | Horowitz | 600/7 |
| 4,842,590 | 6/1989 | Tanabe et al. | 604/282 |
| 4,861,520 | * 8/1989 | Vant Hooft et al. | 600/8 |
| 4,891,165 | * 1/1990 | Suthanthiran | 600/1 |
| 5,059,166 | 10/1991 | Fischell et al. | 600/3 |
| 5,084,002 | * 1/1992 | Liprie | 600/7 |
| 5,111,829 | * 5/1992 | De Toledo | 128/772 |
| 5,147,282 | 9/1992 | Kan | 600/1 |

(List continued on next page.)

FOREIGN PATENT DOCUMENTS

| | | |
|---|---|---|
| 91 02 312 U | 8/1992 | (DE) . |
| 9200776 | * 1/1992 | (WO) .................................. 600/7 |
| WO93/04735 | 1/1993 | (WO) . |

OTHER PUBLICATIONS

Flexmedics, "Nitinol The Material of Choice . . . " 1989.*
M. Friedman et al, Journal of Clinical Investigation, vol. 43, No. 2, pp. 185 et seq., 1964.

(List continued on next page.)

Primary Examiner—John P. Lacyk
(74) Attorney, Agent, or Firm—Blank Rome Comisky & McCauley LLP (57) ABSTRACT

A source wire having a radioactive source at its distal tip is used to treat tissue at a target site within a patient's body by localized in vivo radiation. The source wire is advanced to the target site along the intravascular system of the patient's body from a point external to the body. The source wire is a solid lead of substantially uniform thickness along its entire length, composed of nickel-titanium alloy (nitinol). Alternatively, the wire may be a cable composed of multiple strands of the alloy of substantially uniform thickness throughout the entire length of each strand. The alloy has desired characteristics including flexibility, springiness, slipperiness, mechanical strength and shape memory retention, and the source wire is imparted with certain stressed and unstressed states that depend on flexation of the wire and a prescribed transition temperature. The wire has a diameter suitable for passage into the coronary arteries, and the distal end of the wire is tapered for ease of entry into narrowed portions. The tissue to be treated lies along a portion of the interior surface of a coronary artery which has been subjected to an angioplasty procedure to reduce blockage of the lumen and thereby improve blood flow. However, the angioplasty procedure may itself initiate restenosis. The targeted tissue is irradiated only briefly, with the radioactive source of the source wire centered as much as practicable in the lumen of the coronary artery, as by use a channeled centering balloon. This allows substantially uniform radiotherapy of the targeted tissue.

12 Claims, 4 Drawing Sheets

U.S. PATENT DOCUMENTS

| | | | |
|---|---|---|---|
| 5,199,939 | * | 4/1993 | Dake et al. .............................. 600/8 |
| 5,203,772 | * | 4/1993 | Hammerslag et al. .............. 128/772 |
| 5,213,561 | | 5/1993 | Weinstein et al. ...................... 600/7 |
| 5,242,394 | * | 9/1993 | Tremulis ............................. 128/772 |
| 5,295,995 | | 3/1994 | Kleiman .............................. 606/194 |
| 5,302,168 | | 4/1994 | Hess ........................................ 600/3 |
| 5,308,356 | | 5/1994 | Blackshear, Jr. et al. ........... 606/194 |

OTHER PUBLICATIONS

M. Friedman et al., Arch. Path., vol. 80, Sep. 1965.

H. Bottcher et al, Abstract, Proceedings of the 34th Annual ASTRO Meeting, Nov. 1992.

H. Bottcher et al, Int. J. Radiation Oncology, Biology, Physics, vol. 29, No. 1, pp. 183–186, 1994.

*Weshler et al., Proceedings, 21st Ann. Meeting, European Soc. for Radiation Biol.*, Oct., 1988.

T. Brook et al., Int. J. Radiation Oncology, Biology, Phys., vol. 15, No. 4, pp. 865–870, Oct. 1988.

D. Faxon et al., Amer. Journal of Cardiology, vol. 60, pp. 114–118, Jul. 31, 1987.

S. King III et al., Coronary Arteriography and Angioplasty, pp. 433–460, 1985.

J. Kovalic et al., Int. J. Radiation Oncology, Biology, Phys., vol. 17, No. 1, pp. 77–80, Jul. 1989.

D. Liermann, et al., *Stents: State of the Art and Future Developments*, p. 299 (1995).

Gammamed Centering Intra–Luminal Applicator, p. 926–120 (?), Jan., '90.

Gammamed, Esophagus Applicator, p. 926–100 (?), Jan., '90.

* cited by examiner

METHOD OF TREATING A BODY VESSEL OR DUCT WITH RADIATION FROM WITHIN THE LUMEN

This application is a continuation of U.S. patent application Ser. No. 08/057,322 filed May 5, 1993, now abandoned.

BACKGROUND OF THE INVENTION

The present invention relates generally to radioactive sources used for treatment of tissue in the human body. More particularly, the invention resides in a device, apparatus, and methods for treating tissue by irradiation with a predetermined dose from a radioactive source which is delivered into the body of the patient via a natural or artificial pathway for a very brief treatment interval or fractionated treatment sessions. The device, apparatus and methods of the invention are especially well suited for brachytherapy in which a malignant tumor is exposed to localized in vivo radiation from a pathway within or adjacent the tumor site, or for controlled irradiation of the wall of a blood vessel, particularly coronary arteries or related blood-carrying canals, to condition the interior surface thereof against restenosis.

Brachytherapy, a technique for radiation treatment of malignant tumors, attacks the tumor from within the body. The method typically utilizes a radioactive source wire in which a radioisotope sealed at and substantially integral with the distal tip of a relatively thin wire or cable is delivered via a pathway formed by a catheter or through a natural cavity, duct or vessel of the body directly to the tumor site for localized irradiation. One or more catheters, for example, may be implanted in the patient's body to provide the pathway(s) from a point external to the body to and through the tumor site, so that the interior of the tumor mass is accessible via the catheter(s). The radioactive source, with a radioactivity and that may range from about one curie to about ten curies, is mechanically delivered to the site either by hand feeding the source wire (for low dose and more readily accessible tumor sites) or by means of apparatus known as an afterloader which has a drive system to which the proximal end of the source wire is connected.

Usually, the treatment is fractionated, in that repeated short intervals of treatment are performed, with the source wire being introduced for the irradiation, left in place for the predetermined interval prescribed by the attending oncologist (often after consultation with a physicist who has calculated the size of the tumor, the distance to be traveled by the source, the nature of the pathway to be traversed and likely travel time, and other pertinent factors), and then withdrawn into the afterloader's shielded safe. To permit treatment to be performed through multiple catheters to the tumor site, if deemed appropriate by the oncologist, the afterloader may be provided with a turret for automatic delivery of the source wire in succession to the entry points of the several catheters for automated advancement, treatment and withdrawal in each pathway. The desired treatment time in each case is programmed into the afterloader's control unit.

The treatment regimen may be repeated at regular intervals over a period of many days, weeks or months, and, if successful, results in complete destruction or at considerable shrinkage of the tumor(s). Among the advantages of this type of radiation therapy are exposure of the tumor to fractionated treatment doses of localized radiation so that each individual treatment need only be of extremely short duration to provide the desired effect while reducing the extent of patient exposure and discomfort, and to provide relatively rapid shrinking of the tumor while avoiding prolonged exposure of healthy tissue to radiation.

Because this type of therapy is more applicable to inoperable malignancies deep within the body, the site of the tumor(s) is usually difficult to reach as the source wire is guided through the path provided by the implanted catheter. The catheter itself may be positioned in place using a previously implanted guidewire or "rail" over which it is advanced along a lumen distinct from the lumen of the catheter through which the source wire is advanced and retracted. It is often the case that this pathway is long, extremely narrow and tortuous with numerous bends and turns. It is essential, therefore, that the source wire should be suitably thin, strong and flexible to traverse the pathway. Furthermore, the wire must be adapted to carry a suitably sized radioactive source, i.e., the core which, for high dosage treatments, is typically substantially pure iridium processed in a neutron flux to produce the radioactive isotope Ir-192. Hence, the source wire has the conflicting requirements that it be of sufficiently small diameter and flexibility to traverse the path to and from the tumor, sufficiently strong along with its flexibility to be driven through the pathway without binding or kinking during wire advancement, and with the capacity to deliver a radiation dosage of as much as ten or more curies.

Prior art source wires include cable composed of a multiplicity of tiny strands of stainless steel wire to provide both desired strength and flexibility, but which lack the size or diameter to travel through the smallest sizes of pathways required for brachytherapy treatment of certain tumors, such as in or through the biliary tract or the bronchi of the lungs. Also, cable source wires typically require welding a plug or capsule containing the radioactive source to the distal tip, which creates a point of weakness where fracture may occur. It is imperative, of course, that the source wire be sufficiently sound and reliable to avoid even the remote possibility that it may break and cause the radioactive material portion to be left in the patient's body for a protracted interval of time.

A solid source wire is capable of accommodating the Ir-192 or other source material in a hole formed in the distal tip of the wire to provide better sealing and security of the source material. Also, solid source wire can be produced by specialized techniques in sizes ranging down to from about 0.6 to 0.7 millimeter (mm) diameter to accommodate an Ir-192 source having a dosage or radioactive level or strength of up to about 10 curies. Other conventional source materials include cobalt, cesium, palladium, gold, and iodine. The source wire may be composed of stainless steel, platinum or certain other conventional materials of suitable flexibility.

For low dose sources in particular, such as one curie or slightly higher, the source material may be installed and the entire source wire then subjected to processing in a nuclear reactor to impart the desired level of radioactivity to the source material. This is an acceptable procedure where the half-life of the wire material is considerably less than that of the source material, so that the radioactivity of the wire material itself is sufficiently dissipated to permit it to be used within a few days after activation. Platinum wire, for example, is suitable for that purpose. For higher dose sources, the source material alone is subjected to the neutron flux and subsequently assembled in the wire by means of shielded, remotely controlled handling and manipulating techniques.

Recently, it has been found that radioactive irradiation of the interior wall surface of blood vessels in general and the coronary arteries in particular with a low dose source for a very brief interval following treatment of the vessel for removal or compression of occluding, lagging, or lacking material such as plaque, enjoys marked success in preventing restenosis. Restenosis is a recurrence of the stricture or narrowing of the vascular lumen or heart valve following surgery or other treatment for removal or reduction of an occlusion, or from related trauma. For example, cardiac patients who have been treated by balloon angioplasty, artery interior wall scraping, laser removal of plaque, by-pass surgery, and other conventional techniques for treating stenosis or occlusion of the blood vessels either because of or in avoidance of myocardial infarction, have been found to experience high incidence of restenosis.

Approximately one-third of the patients who have had arteries unblocked suffer restenosis about six months later, requiring that the procedure be redone. And in fact, repeating the procedure appears to increase the trauma to the smooth muscle cells and to speed their regrowth. Fifty percent of the patients experience some form of re-occlusion of the treated vessel. While a repeat procedure may not be required for all of those patients, some re-occlusion does occur. The remaining 50% of the patients seem to suffer no re-occlusion, and there is no single explanation for it.

The fact that one-third of all patients require re-treatment, at substantial additional cost and with potential loss of life raises questions concerning the significance of a 95% success rate for the initial unblocking procedure. Moreover, if a second re-occlusion occurs, the next procedure performed on the patient is likely to be open heart surgery.

Restenosis, then, is really an injury response mechanism to the unblocking procedure, at least for some substantial percentage of the patients. Attempts to correct the restenosis problem by use of drugs have not been successful.

Irradiation of the vessel wall with a radioactive source appears to alleviate the problem in tests conducted on rabbits and rats, but creates a new problem in that the source wire must be sufficiently thin, flexible and strong to be capable of placement in the offending arteries. This is by no means a simple task, because of the small size of the vessels, the difficulty in reaching the target area through the artery as a consequence of the small size of the target and the tortuous pathway involved, and especially the susceptibility of the patient to a heart attack if the critical vessel is blocked for an inordinate time during performance of the treatment.

The problems involved are similar to, if not greater than, those encountered in treatment of tumors by brachytherapy as described above. It is a principal object of the present invention to provide new and improved source wires, apparatus and methods for in vivo, localized, internal radioactive treatment of selected tissue in the human body.

The cost of treatment for heart attack victims is staggering, and is among the procedures being addressed in a strong effort toward cost containment by treatment centers and other care providers. Of course, if treatment is unsuccessful, inadequate or untimely, the cost is even greater—in loss of life. Therefore, it is another important object of the present invention to provide improved and lower cost means and methods for treating cardiac patients to avoid restenosis of the veins and arteries, and even of the heart valves, following procedures used to open a blocked or partially blocked or inoperative blood passageway.

SUMMARY OF THE INVENTION

According to the present invention, a new and improved radioactive source wire is provided for use both in brachytherapy and cardiac treatment for the purposes described above. In particular, the source wire is composed of a nickel-titanium alloy known commercially as nitinol which has the desired properties of flexibility, springiness, slipperiness, mechanical strength and super-elasticity, and which returns to a straight shape after it is withdrawn from the narrow tortuous pathway through which it was driven for purposes of treatment. The radioactive source material, such as Ir-192 (iridium isotope) spheres, is loaded in an axial hole in the distal tip of the wire, which is then sealed with a nitinol plug as by welding. The nitinol source wire is readily returned to the drive system of the afterloader without likelihood of kinks or bends, for subsequent use in another or other procedures of the same type.

The wire is composed of a shape memory alloy, the nickel/titanium alloy nitinol being preferred, possessing super-elastic properties and the capability, at proper temperature, of transforming from an unstressed austenitic state (being a straight configuration) to a stress induced martensitic state and the capability of returning to the austenitic state when the externally induced stress is removed. The deformations encountered in tortuous pathways are fully recovered without permanent plastic deformation, and the material transforms to the stable austenitic state for storage or spooling with no permanent deformation from the prior use.

Nitinol has been used commercially in bendable frames for lenses (eyeglasses). It has also been used in the past for rails (guidewires) that are employed in various parts of the body by placement through a lumen to define a selected site as a means to transport and retrieve items to and from that site. In this way, the rail dispenses with the need to relocate the selected site repeatedly, such as for placement of catheters. However, to our knowledge, there has been no suggestion that nitinol would serve a useful purpose as a source wire for radioactive source material.

The procedure for which the nitinol source wire is used may be a brachytherapy application or a coronary radiotherapy application. The same basic afterloader drive system is used for both applications, although the machines themselves are somewhat different. For example, the brachytherapy (oncology) afterloader is more complex only because of the large variety of targets (tumors at sites possibly anywhere in the body, versus targets at or in the region of the heart for the coronary machine), and up to about 20 channels versus only one channel required for the coronary radiotherapy machine. The radioactivity shielded safe is larger on the oncology machine because the source is of greater radioactivity level. Also, in the coronary machine it is not necessary to use a turret, or at maximum, a two-position turret, whereas the turret of the brachytherapy afterloader has a number of positions corresponding to the array of channels available for delivery of treatment. The basic structure of each machine may be entirely conventional.

In the coronary radiotherapy treatment procedure of the invention, the afterloader equipment is adapted to advance a dummy wire (non-radioactive) through the implanted catheter to the target site under visual observation such as fluoroscopy, after which the dummy wire is retracted, and the source wire is then automatically advanced to the target site through the catheter for localized irradiation of the vessel wall over a very brief period of time that depends on the radioactivity dosage prescribed by the attending physician. The dummy wire has an opaque tip marker to facilitate the fluoroscopic observation, and the precise location of the target area along the pathway is calibrated in the afterloader according to the measured distance of travel by the dummy wire. The treatment is performed automatically by remote operation of the afterloader which is located in a radiation-shielded room where the patient is placed for the treatment.

A treatment catheter is coupled to the end of the afterloader connector and deployed over a rail guidewire to the target site for ultimate delivery and retraction of the radioactive source. In the case of coronary radiotherapy, the source material in the source wire must be centered radially in the lumen of the coronary artery to the maximum practicable extent to provide uniform irradiation in the sense of subjecting tissue along each segment of the interior surface portion of the length of the artery wall that has been subjected to angioplasty, surgery, or other treatment for removal or reduction of an occlusion thereat, to a radiation dosage with predetermined therapeutic range of efficacy in a circumferential cross-sectional, band about the source material encompassing the artery wall, over a prescribed time interval, to achieve maximum results, i.e., to prevent restenosis in that treated portion of the length. A non-centered source could deliver too little radiation to one side of the artery interior wall, resulting in no effective treatment of that region, and too much to the other side, resulting in possible injury to that portion.

SUMMARY OF THE DRAWINGS

The above and still further objects, features and attendant advantages of the present invention will become apparent from consideration of the following detailed description of certain presently preferred embodiments and methods of the invention, taken in conjunction with the accompanying drawings, in which.

DETAILED DESCRIPTION OF THE PREFERRED EMBODIMENT AND METHOD

Figure 1:
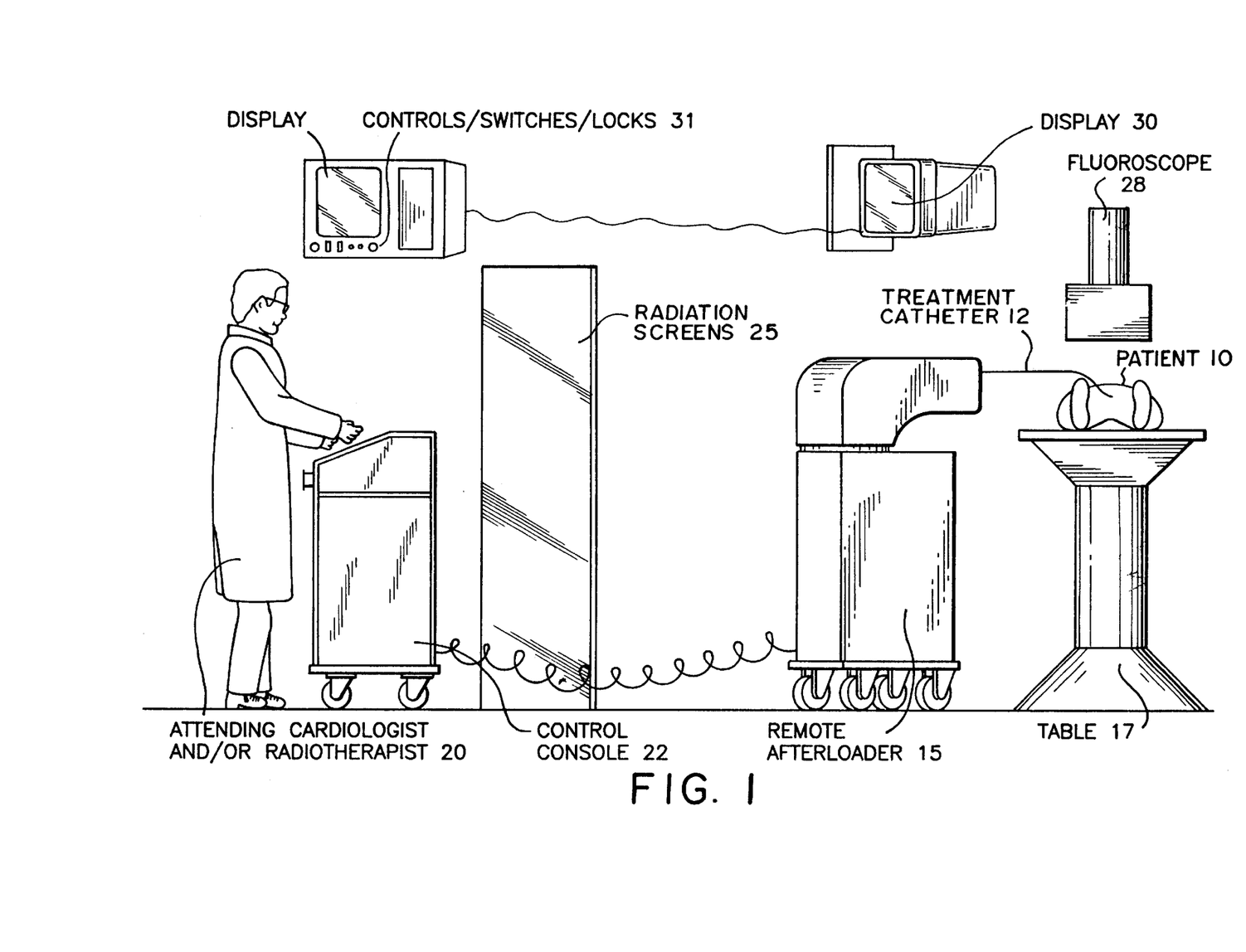
FIG. 1 is a simplified view of a typical arrangement for implementing a procedure with a brachytherapy system or a coronary radiotherapy system according to the present invention.

Referring to FIG. 1, the invention in one of its aspects is used in treatment regimens provided by a brachytherapy system or a coronary radiotherapy system. In practice, the patient 10 is moved into a radiation-shielded treatment room where the procedure will be performed. A treatment catheter 12 is implanted in the patient, and, in the coronary or cardiac procedure is also coupled to a connector of the drive system for the remote afterloader 15. The drive system, and indeed, the entire afterloader may be completely conventional for the brachytherapy application, and would require only a few changes for the cardiac application.

It will be understood that while both uses are described in this specification, in the typical case, the patient will go through only one of the two procedures. Also, separate afterloaders and treatment rooms would be provided for the two different applications. The description of both procedures here is solely for the sake of convenience, and because many aspects of the present invention are applicable to both types of treatment.

For treatment, the patient 10 is placed in a supine or a prone position on a table 17, with the afterloader 15 placed in close proximity to allow the source wire of the afterloader to be deployed through the treatment catheter into the selected target site in the patient's body. The afterloader is controlled by the attending physician, an oncologist in the case of brachytherapy treatment or a cardiologist in the case of cardiac treatment, and/or by a radiotherapist 20 from a control console 22. In practice, the control console may be in the treatment room where low dose radioactivity treatment is being performed, but shielded with the attendant by a set of radiation screens 25, or may be located outside the shielded treatment room for high dose radioactivity treatments.

A fluoroscope 28 is positioned above the patient, although its use would usually be required only for the cardiac treatment. A video camera and display monitor 30 are positioned to allow attendant 20 to view the patient, with equipment including display controls 31 positioned within easy access to the attendant.

The method used in performing brachytherapy is entirely conventional, and hence, only portions of it will be described here in those portions of the text where appropriate. Description of the method and certain specialized apparatus employed for the cardiac treatment will be described presently. First, however, it is desirable to describe aspects and features of the preferred embodiment of a source wire which, except for radioactive dosage requirements, may be used for either procedure.

According to the preferred embodiment of the invention, the source wire is an assembly of an elongate wire composed of a nickel/titanium alloy commercially marketed as nitinol. Nitinol is available, for example, from Shape Memory Alloys of Sunnyvale, California. The material is described, for example, in U.S. Pat. No. 4,665,906. For purposes of the source wire application according to the invention, the nitinol in the form of a wire is stored in its austenitic state (below the transition temperature, discussed below), characterized by a straightened shape, and when used is flexed to put it in a stress-induced martensitic state (above the transition temperature), which is characterized by superelasticity. When the wire is formed, the process, which involves several separate treatments at high temperature, produces a transition temperature of the material between its austenitic state in which it is ductile, to the stress-induced martensitic state. In source wire of the invention, the nitinol is always used for treatment at a temperature above the transition temperature, which is typically 150° C.±50° C., for example, and is in the austenitic state except when the wire is in flexation at which it is in the stress-induced martensitic state. This is the case for the nitinol wire used in either of these applications, where it is bent and flexed as it moves through a tortuous path in the human body in the brachytherapy treatment or cardiac treatment procedure.

The transition temperature may be varied somewhat as a function of the manner in which the nitinol wire is processed, especially its heat treatment. For example, in one form in an austenitic state the wire material was floppy, which did not adversely affect cycling tensile strength or shear strength. In the preferred form the nitinol wire has a sufficient memory aspect to retain straightness despite a capability to be flexed.

For purposes of assuring retention of its desired properties in that state, such as the properties of high flexibility, springiness, slipperiness and mechanical strength, the nitinol wire is heat treated while it is being processed to form wire of the desired diameter for use in the brachytherapy and coronary radiotherapy applications of the invention. As with stainless steel rods and wires, nitinol can be drawn and successively redrawn to progressively smaller diameters.

Because the manufacturing process can affect the wire's properties, it is important to verify metallurgical specifications as part of the testing of the wire for performing validations, including basic factors such as ultimate tensile strength. Cycling of the wire (i.e., putting it through tests in which it is used and reused in the intended manner for the application) is important to detect otherwise unseen characteristics that may adversely affect its performance, such as case hardening due to grinding, and to assure absence of lot-to-lot variations.

Three different processes were employed to produce the nitinol wire for use in source wire according to the invention. It was necessary both to produce the wire in its final form (i.e., dimensional including diameter and length) and to provide it with a cavity in which radioactive source material would be retained. In particular, an axial hole is formed at the distal end of the wire to house the source material, which would subsequently be sealed to prevent particulate loss and contamination.

One process of producing the wire with an axial hole at its tip involved drilling a hole in an oversize wire or rod, followed by repeated drawing of the wire through progressively smaller dies until the desired wire diameter and hole depth were achieved. During the drawing stages the depth of the hole underwent lengthening, as would be expected, so it is necessary to calculate the desired final depth and from that, determine the depth of initial drilling of the hole. Wire diameter of 0.023 inch and hole diameter of 0.014 inch is preferred. This hole drilling and drawing process to provide the final form of the wire and desired properties was performed for the assignee of the present application by the Raychem Corporation of Menlo Park, Calif.

A second process, also performed by Raychem Corporation, produced a similar form of wire which constitutes a thin-walled nitinol tube clad over a nitinol backbone wire running substantially the entire length of the tube except for a portion at the tip. This portion provides the hole of desired depth to house the source material. Other dimensions of the tube/backbone wire are substantially the same as those described above for the drilled hole/drawdown version of the wire. A slightly greater outer diameter of 0.022 inch resulted from this process.

A third process, which was used only to produce the axial hole in the tip of a nitinol wire of the final desired diameter, involved the use of electrical discharge machining (EDM) performed by Mega Technology EDM, Inc. of Norcross, Ga. In contrast to the other processes, the EDM process has tended to produce a hole wall of somewhat varying thickness. In any event, however, the EDM process did produce a hole of desired diameter and depth in the end of the wire without need for further drawing.

Figure 4:
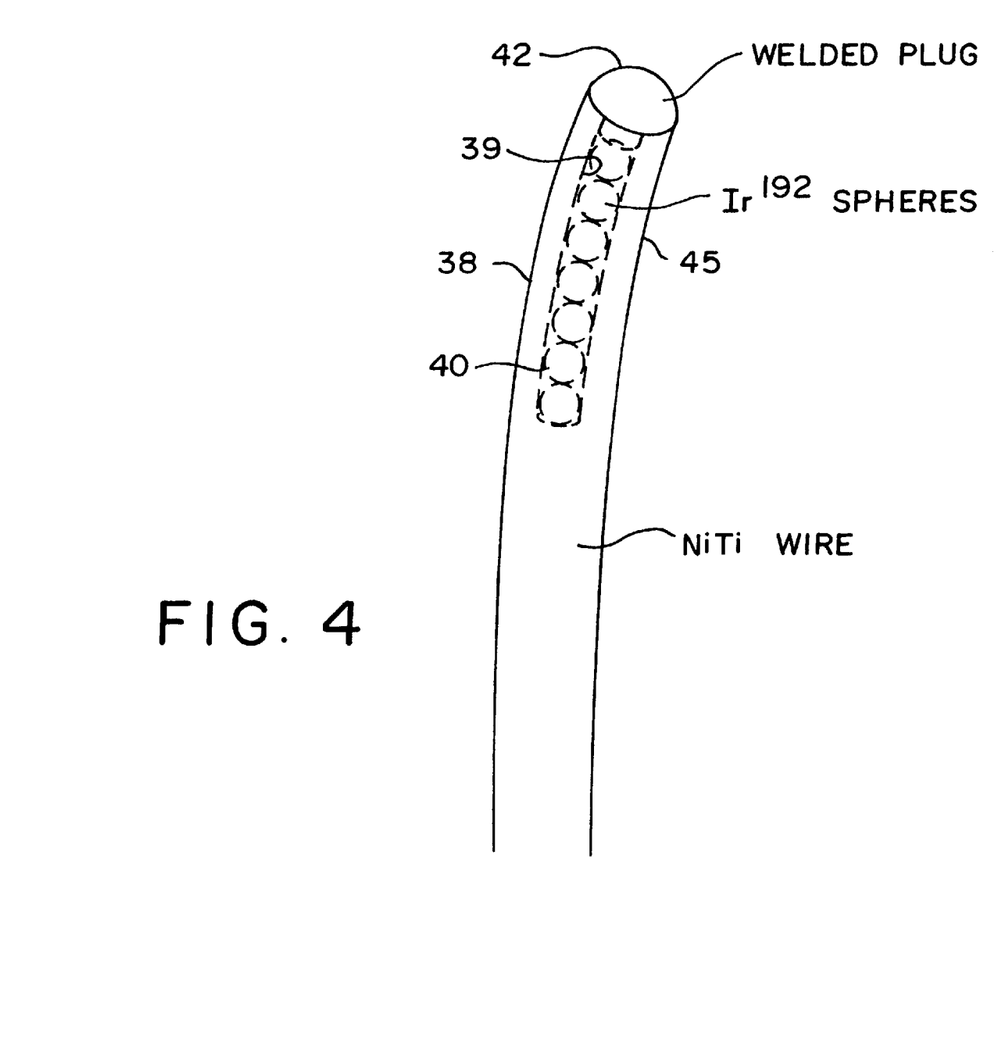
FIG. 4 is a fragmentary sectional side view of the source wire showing an exemplary assembly of the radioactive source material and special wire material according to the invention.

A fragmentary portion of the final source wire is shown in the side sectional view of FIG. 4. The nitinol elongate wire 38 with axial hole 39 in its distal tip is loaded with radioactive source material such as iridium isotope Ir-192 spheres 40 of slightly smaller diameter than that of the hole 39. The radioactivity level of the total source material in the wire is preferably about one to two curies (a low dose wire) for the cardiac application, and from that dose up to about 10 curies (a high dose wire), depending on physician-prescribed dosage, for the brachytherapy application.

After loading the source material, a nitinol plug 42 of preferably rounded shape is inserted into hole 39 to tightly cap it. The plug is then welded to seal the hole against loss of any source material. The source material may be enriched Ir-192, and in any event is substantially pure iridium converted to radioactive form by treatment in a nuclear reactor in a known manner. The radioactive spheres are assembled in the nitinol wire and the hole is sealed with the welded plug by manipulations performed using remote manipulators in an assembly area.

A feature of the preferred embodiment of the source wire is that it may be tapered down at the distal end to provide even greater flexibility in reduced size at the point of delivery of the dosage to the target which is to be irradiated. A somewhat larger diameter of the wire up to the point at which the taper begins is useful to provide the column strength sufficient for drivability of the wire by the afterloader. For example, in the embodiment of FIG. 4 the distal end 45 of the wire may be tapered over the last six inches to the tip, by drawing that portion through an appropriately sized die. The tapering process would be performed prior to loading radioactive source material.

If a multi-strand cable were used in place of a solid wire for the source wire, the cable can similarly be tapered. This is accomplished by tapering every strand at the distal end, so that when the strands are is twisted to produce the final form of the cable, it has a rat-tail shaped taper. Although it is not the preferred mode of a source wire, the multi-strand cable form may be assembled with a small capsule containing the radioactive source material, by welding the capsule to the distal tip of the cable. Each strand may have an extremely small cross-section, e.g., 0.001 inch, so that it bends easily, making the overall cable very flexible. Such cables have been produced without taper in stainless steel, but a form used in accordance with the present invention would employ nitinol strands.

By way of comparison, a nitinol solid wire has almost twice the column strength of a multi-strand stainless steel cable of corresponding diameter. Multiple strand cable ordinarily has a slight advantage in flexibility, but the nitinol material tends to reduce that advantage by virtue of its flexibility, even as a solid lead. Such flexibility is especially important in the applications described herein. Insufficient flexibility can cause the wire to develop small kinks as it travels through curves in the catheter, and the kinks become of greater width in any short section of the wire than the width of the catheter lumen. Consequently, the wire will lock in the catheter, perhaps so much so that it becomes immovable in either direction. This is completely unacceptable where a radioactive source wire is being used.

In the method of the invention, a treatment catheter 12 (FIGS. 1, 3) is implanted in the patient to provide the pathway to be traveled by the source wire, and the wire is advanced (or withdrawn) in that pathway through the catheter during the treatment procedure, whether for brachytherapy or for coronary radiotherapy. Of course, the selected target is different depending upon application.

Figures 2, 3, 3A:
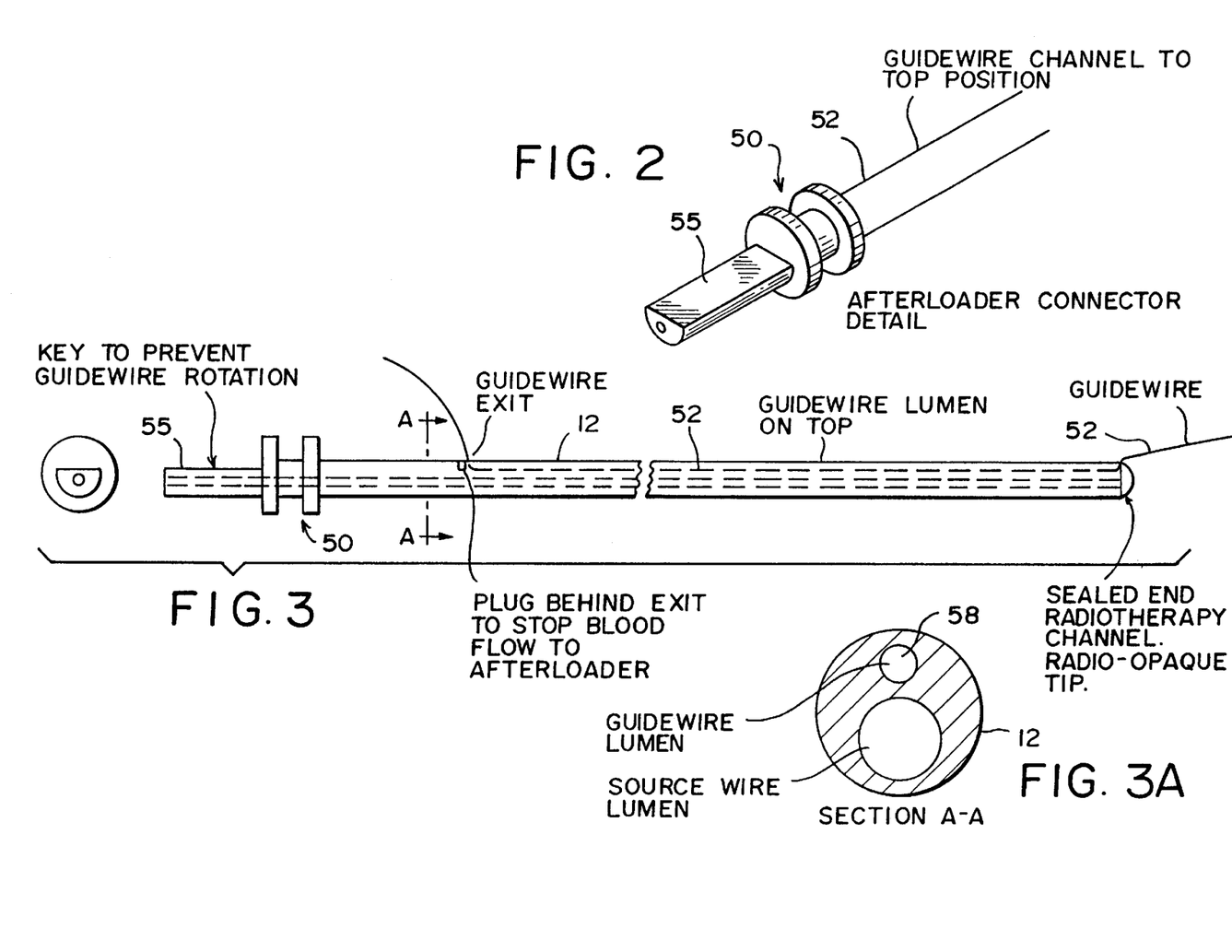
FIG. 2 is a fragmentary, perspective view of a catheter, rail, and source wire connected at the proximal end to the afterloader drive connector.
FIG. 3 is a simplified side view of the system of FIG. 2.
FIG. 3A is a sectional view through the lines A—A of FIG. 3.

In the cardiac application, the catheter is also coupled to the afterloader connector 50 by a guidewire or rail 52 which extends to the target site. The catheter for that application may be provided with small channels to allow some blood flow (perfusion) therethrough. The catheter 12 is placed over the rail 52 which is hooked into the connector for the afterloader as well. The afterloader connector 50 is also coupled to the turret. A key 55 is used to lock the coupling in place and prevent the catheter and the rail from undergoing rotation.

Since the rail lumen 58 (FIG. 3A) is at the top of catheter 12, the key 55 on the afterloader coupling 50 locks the catheter against rotation. If the catheter were allowed to rotate, the rail (guidewire) 52 would begin uncontrollable spinning because of the eccentricity of its lumen 58 in the catheter. Orientation of the guidewire channel is also extremely important, and is maintained by the key.

The cardiac application of the radioactive source wire is extremely size sensitive. Among critical issues for that application are flexibility for access through the fine and tortuous pathways to the very fine and remote blood vessels, and size for entry into the vessels, and radial centering of the radioactive source in the lumen of the vessel.

A suitable level of radioactivity (dosage) for the source in this application is one curie, and such a source would be maintained centered in the lumen of the vessel in each segment of the affected length thereof for a time interval sufficient to produce, say, 1,000 to 1,500 rads, which is a radiation dosage in the therapeutic range of efficacy over the particular time interval at one millimeter distance from the blood vessel wall or heart valve wall to the surface of the source. Radioactivity delivered to the wall surface depends on factors such as the length of source, the length of the lesion and the curie level on the day the treatment is performed, and the length of time of the treatment.

Without perfusion, the patient can only tolerate one to one and a half minutes of total occlusion in the target area, which means that the treatment must be stopped before the limit is reached, the attending personnel then return, the balloon is deflated to allow the heart (or the portion being treated) to reoxygenate. After an interval of, say, three to five minutes, the treatment procedure is recommenced to apply the remaining dosage required to irradiate the target area by redeployment of the source wire and the centering balloon.

It is also imperative to provide centering of the distal tip of the wire, and more specifically, the radioactive source (which, as described above, is assembled into an axial hole in the distal tip of the wire) in the lumen of the vessel, to provide substantially uniform irradiation of the tissue in a band of efficacy about the source. The need for centering is still essential but of somewhat less concern with a small diameter artery because the two may be substantially the same diameter. For example, one side may be 2½ mm and the other may be 2 mm. The need to center exists to avoid a hot spot on one side and a cold spot on the other. Preliminary results also indicate that a failure to obtain a certain threshold of radiation on the vessel wall, about 1,000 rads, will result in no discernible prevention of restenosis.

Figures 5A, 5B:
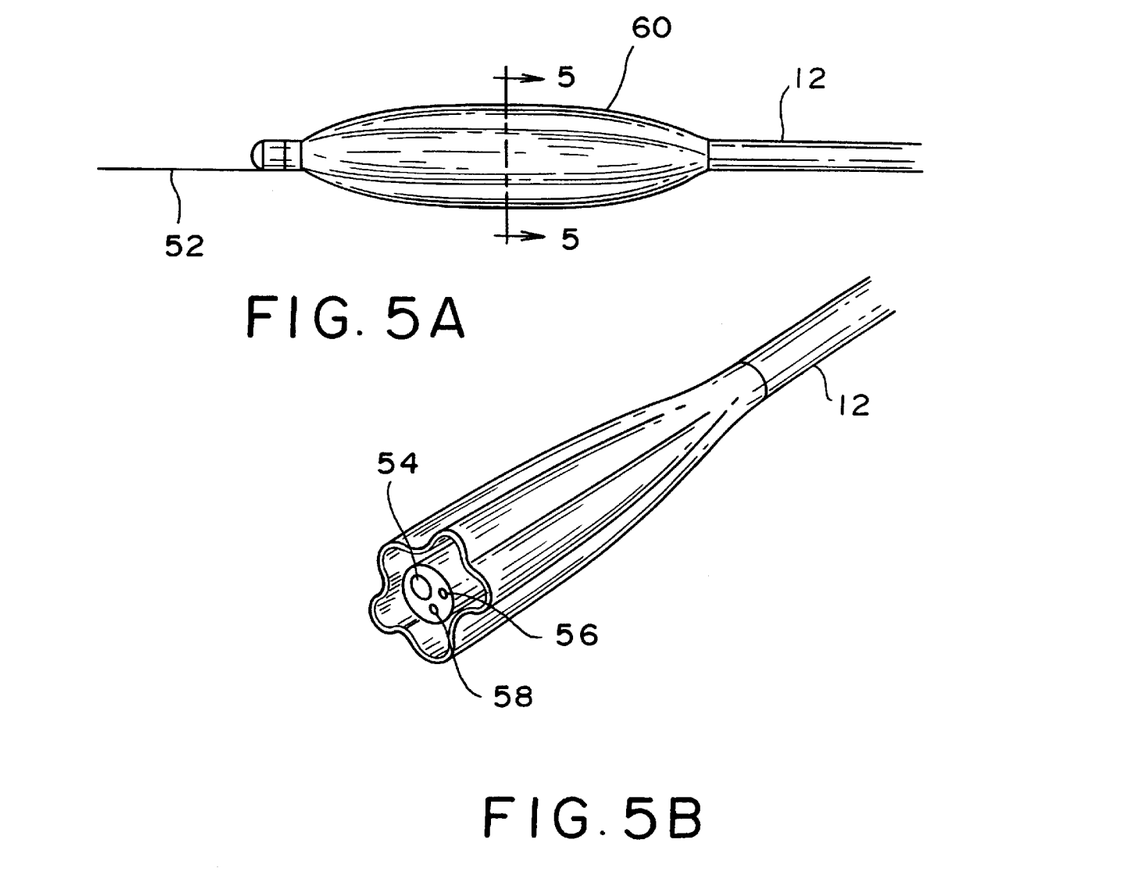
FIG. 5A is a plan view of a centering balloon according to the present invention.
FIG. 5B is a perspective sectional view of the centering balloon of FIG. 5A taking at line 5—5.

In the preferred embodiment, an inflatable balloon 60 (FIG. 5A) is provided in the catheter for centering the source tip of the source wire. A dose of 1,000 to 1,500 rads drops off according to the inverse square of the distance, so that a distance of 5 mm from the vessel wall to the source (actually the tip of the source wire), causes the field strength to drop off sharply, with concomitant loss of threshold. The treatment catheter may include, in addition to the working treatment (radiotherapy) channel 54, the rail (guidewire) channel 58, an inflation channel for the centering balloon 56 (FIG. 5B). Segmented or scalloped balloons, or otherwise channeled balloons may be used, together with a channeled catheter or alone, to permit some flow-by of blood sufficient to avoid complete blockage during treatment.

For treatment at the bottom of the heart, a scalloped catheter with no balloon is preferred. In that situation, centering of the source within that treatment area with some blood flow-by capability is achievable without need for a balloon.

A different type of centering mechanism from a centering balloon may be used, and in that event could be of a type and shape that would permit sufficient blood flow so that the procedure need not be stopped before the treatment regimen is completed. The disadvantage of using a different mechanism is principally in the means for deployment. Balloon inflation and deflation in a catheter is in and of itself an entirely conventional technique and has a proven record of safety.

The irradiation procedure is preferably performed very soon after the balloon angioplasty (PTCA) or other unblocking procedure is completed on the vessels. The rail (guidewire) is left in place during the period of treatment because it allows a rapid return to the target. Since the rail is tiny, at 0.014 inch, it does not seriously impede blood flow. Initially, the rail is steered into the part of the heart being targeted, using a fluoroscope, becomes the first component in and the last out.

If not installed properly, a branching effect can occur. Thus, the catheter and subsequently the source wire must be advanced to the desired branch via the rail. The catheter is placed over the rail, and in available size ranges, is capable of moving through vessels or ducts as small as two mm in diameter.

Lumen diameter of the artery dictates the choice of treatment catheter as well as the radioactivity dose. If it is determined that the dose should be 1,450 rads, for example, that value is entered on the control console of the afterloader, or other factors may be entered by which a microprocessor in the control console may calculate the dose according to location of the target, size of lumen, center of the lumen (distance to the interior wall surface), curie rating per day, and other known factors.

A fail-safe function of the afterloader senses patient problems when the coronary radiotherapy is administered. In the event that the patient is experiencing pain or other difficulties, the source wire is promptly drawn back and the balloon is deflated and the patient's heart is allowed to reoxygenate. The target location is marked with a dummy wire deployed from the afterloader. The control console of the afterloader enables programming of the desired functions. A one to one and one-half minute interval is timed by the afterloader, the procedure halted at that point, the source wire is retracted into the safe. The afterloader retains all necessary data such as the dose given and the dose given on transit to and from the point at which initiated, or transit dose, and treatment is re-commenced after a break of two or three minutes.

Although a preferred embodiment and method of the present invention has been described herein, it will be apparent from the foregoing description to those skilled in the field of the invention that variations and modifications of the invention may be implemented without departing from the spirit and scope of the invention. Accordingly, it is intended that the invention shall be limited only to the extent required by the appended claims and the rules and principles of applicable law.

What is claimed is:

1. A method of treating the wall of a blood vessel, comprising:

advancing a guidewire to a treatment site in the blood vessel;

advancing a catheter having a guidewire lumen over the guidewire to the treatment site; and advancing a radioactive source through a working lumen of the catheter, the distal end of the working lumen being located proximal to the distal tip of the catheter.

2. The method of claim 1, wherein the step of advancing a catheter comprises advancing a balloon catheter having a separate lumen for inflating a balloon of the balloon catheter.

3. The method of claim 2, wherein the step of advancing a balloon catheter includes utilizing a scalloped balloon secured to the catheter, with said separate lumen for inflating lobes of the scalloped balloon.

4. The method of claim 2, wherein the step of advancing a balloon catheter includes utilizing a segmented balloon secured to the catheter, with said separate lumen for inflating segments of the segmented balloon.

5. The method of claim 2, wherein the step of advancing a balloon catheter includes utilizing a channeled balloon secured to the catheter, with said separate lumen for inflating the channeled balloon.

6. The method of claim 1, wherein the step of advancing a radioactive source comprises advancing the radioactive source through a proximal coupler for entry into said working lumen.

7. The method of claim 6, wherein the step of advancing the radioactive source is performed using an afterloader to which the radioactive source is connected through said coupler to selectively drive the radioactive source into the working lumen to a predetermined depth within the catheter.

8. The method of claim 7, including keying said coupler to inhibit rotation of the catheter about its axis.

9. The method of claim 1, wherein the step of advancing the radioactive source through said working lumen of the catheter is performed by advancing a wire having said radioactive source secured at its distal end.

10. The method of claim 9, including using a super-elastic wire as the wire to which said radioactive source is secured.

11. The method of claim 1, including using a radioactive source of predetermined activity level and leaving the source in place, after advancement to the treatment site, for a predetermined time interval sufficient to deliver a prescribed radiation dosage of from about 1,000 rads to about 1,500 rads to tissue in the blood vessel wall in proximity to the vessel lumen at the treatment site.

12. The method of claim 11, including withdrawing the radioactive source from said working lumen of the catheter upon delivery of said prescribed radiation dosage.

* * * * *